US010751943B2

(12) United States Patent
Grbic et al.

(10) Patent No.: US 10,751,943 B2
(45) Date of Patent: Aug. 25, 2020

(54) PERSONALIZED CREATION FROM MEDICAL IMAGING

(71) Applicant: Siemens Healthcare GmbH, Munich (DE)

(72) Inventors: Sasa Grbic, Princeton, NJ (US); Michael Suehling, Erlangen (DE); Tommaso Mansi, Plainsboro, NJ (US); Ingmar Voigt, Erlangen (DE); Razvan Ionasec, Nuremberg (DE); Bogdan Georgescu, Plainsboro, NJ (US); Helene C. Houle, San Jose, CA (US); Dorin Comaniciu, Princeton Junction, NJ (US); Charles Henri Florin, Trenton, NJ (US); Philipp Hoelzer, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 245 days.

(21) Appl. No.: 14/833,165

(22) Filed: Aug. 24, 2015

(65) Prior Publication Data
US 2017/0057169 A1    Mar. 2, 2017

(51) Int. Cl.
*B29C 64/386* (2017.01)
*A61F 2/24* (2006.01)
(Continued)

(52) U.S. Cl.
CPC .......... *B29C 64/386* (2017.08); *A61F 2/2415* (2013.01); *A61F 2/06* (2013.01);
(Continued)

(58) Field of Classification Search
CPC . B29C 67/0088; B29C 64/386; B29C 64/393; A61F 2/2415; A61F 2240/004;
(Continued)

(56) References Cited

U.S. PATENT DOCUMENTS

| 8,442,780 B2 * | 5/2013 | Lu | G01N 3/12 600/587 |
| 2005/0113961 A1 * | 5/2005 | Sabol | A61B 5/055 700/182 |

(Continued)

FOREIGN PATENT DOCUMENTS

WO    WO 2015009235 A1 *  1/2015  ............... A61F 2/20

OTHER PUBLICATIONS

U.S. Appl. No. 14/539,051, filed Nov. 12, 2014.
(Continued)

*Primary Examiner* — Rocio Del Mar Perez-Velez
*Assistant Examiner* — Brian T McMenemy

(57) ABSTRACT

In personalized object creation, for implants, medical imaging is used to derive a model personalized to a patient. The model may be of a dynamic structure, such as part of the cardiovascular system, and is used to print the implant itself. The model may be used to print a mold to create the implant, a scaffold on which to grow tissue, and/or tissue itself. In another or additional approach, the medical imaging information is used to determine tissue properties. Differences in a material property of the anatomy is mapped to different materials used by a multi-material 3D printer, resulting in a printed object reflecting the size, shape, and/or other material property of the anatomy of the patient.

18 Claims, 4 Drawing Sheets

(51) Int. Cl.
  *B33Y 30/00* (2015.01)
  *B33Y 50/02* (2015.01)
  *A61F 2/06* (2013.01)

(52) U.S. Cl.
  CPC ........... *A61F 2/2409* (2013.01); *A61F 2/2418* (2013.01); *A61F 2230/0006* (2013.01); *A61F 2240/002* (2013.01); *A61F 2240/004* (2013.01); *A61F 2250/0039* (2013.01); *B33Y 50/02* (2014.12)

(58) Field of Classification Search
  CPC .. A61F 2/2418; A61F 2250/0039; A61F 2/06; A61F 2240/002; A61F 2/2409; A61F 2230/0006; G05B 19/4099; B33Y 50/02
  See application file for complete search history.

(56) References Cited

U.S. PATENT DOCUMENTS

| | | | | |
|---|---|---|---|---|
| 2008/0242977 A1* | 10/2008 | Sirohey | ............. | A61B 5/02007 600/425 |
| 2009/0163810 A1* | 6/2009 | Kanade | ................... | G06T 7/344 600/443 |
| 2012/0269407 A1* | 10/2012 | Criminisi | ................... | G06T 7/77 382/128 |
| 2014/0265035 A1* | 9/2014 | Buser | .................... | B29C 64/386 264/401 |
| 2014/0312535 A1* | 10/2014 | Dikovsky | ........... | A61F 2/30942 264/401 |
| 2015/0025666 A1* | 1/2015 | Olivieri | ................... | G06F 17/50 700/98 |
| 2015/0209162 A1* | 7/2015 | Verschueren | ............. | A61F 2/07 623/1.15 |
| 2015/0250934 A1* | 9/2015 | Min | ..................... | A61M 1/1053 623/3.11 |
| 2015/0269282 A1* | 9/2015 | Nelaturi | ................... | G06F 17/50 700/98 |
| 2015/0313577 A1* | 11/2015 | Duric | ....................... | A61B 8/15 600/438 |
| 2015/0342720 A1* | 12/2015 | Koc | ....................... | C12M 21/08 623/1.41 |
| 2016/0129637 A1* | 5/2016 | Zhou | ...................... | B33Y 50/00 700/98 |
| 2016/0175052 A1* | 6/2016 | Kumar | ................. | A61N 5/1037 600/407 |
| 2016/0191887 A1* | 6/2016 | Casas | ................. | H04N 13/0011 348/47 |

OTHER PUBLICATIONS

Grbic, Sasa, et al. "Image-based computational models for TAVI planning: From CT images to implant deployment." Medical Image Computing and Computer-Assisted Intervention—MICCAI Springer Berlin Heidelberg, pp. 395-402, 2013.

Grbić, Saša, et al. "Complete valvular heart apparatus model from 4D cardiac CT." Medical Image Computing and Computer-Assisted Intervention—MICCAI 2010. Springer Berlin Heidelberg, Dec. 21, 2011.

Ionasec, Razvan Ioan, et al. "Patient-specific modeling and quantification of the aortic and mitral valves from 4-D cardiac CT and TEE." Medical Imaging, pp. 1636-1651, Sep. 2010.

Murphy, Sean V., and Anthony Atala. "3D bioprinting of tissues and organs." Nature biotechnology 32.8: 773-785, Aug. 2014.

* cited by examiner

PERSONALIZED CREATION FROM MEDICAL IMAGING

BACKGROUND

The present embodiments relate to personalized objects created from medical imaging. Many diseases are currently treated with replacement or repair of the diseased anatomy. In some cases, a device (e.g. scaffold for aortic aneurisms or artificial aortic valve for valve replacements) is implanted to mimic the function of the original anatomy. Most of the devices currently available come in a discrete set of options, such as aortic valve replacement devices being available in three options that vary in size (e.g., 3 mm gaps between models). As the anatomy of patients exhibits a large variety of distinct shapes and sizes, the limited number of discrete device options may not be ideal for some patients. For complex anatomical deformation, especially in pediatric cases, an appropriate device may not be available.

Personalized geometrical models of various anatomical parts may be obtained from medical images. These models may be used to assist in diagnosis, therapy planning, guidance, monitoring, or training. The geometrical models may be used to three-dimensionally (3D) print a patient-specific object. The printed objects may assist in visualization or understanding, but have limitations since the object merely represents the shape and/or size of anatomy.

BRIEF SUMMARY

By way of introduction, the preferred embodiments described below include methods, systems, instructions, and computer readable media for personalized object creation. For implants, medical imaging is used to derive a model personalized to a patient. The model may be of a dynamic structure, such as part of the cardiovascular system, and is used to print the implant itself. The model may be used to print a mold to create the implant, a scaffold on which to grow tissue, and/or tissue itself. In another or additional approach, the medical imaging information is used to determine tissue properties. Differences in a material property of the anatomy is mapped to different materials used by a multi-material 3D printer, resulting in a printed object reflecting the size, shape, and/or other material property of the anatomy of the patient.

In a first aspect, a method is provided for personalized implant creation. A medical imaging system acquires scan data representing an anatomic structure of a patient. The anatomic structure dynamically varies over time in response to a physiological cycle of the patient. A model of the anatomic structure is created from the scan data. A three-dimensional printer prints an implant-related device based on the model of the anatomic structure of the patient.

In a second aspect, a system is provided for personalized implant creation. A medical imaging system is configured to scan a patient. A processor is configured to create a surface model of anatomy of the patient from the scan and construct a volumetric model based on the surface model. A three-dimensional (3D) printer is configured to print an object based on the volumetric model.

In a third aspect, a system is provided for personalized object creation. A medical imaging system is configured to scan a patient at different times where anatomy changes between the different times. A processor is configured to estimate variation of a material property of the anatomy based on the change represented by the scans. A multi-material three-dimensional (3D) printer is configured to print an object using different materials emulating the variation of the material property of the anatomy.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A personalized device is created from medical imaging and manufactured with a 3D printer. A 3D medical image or volume is used to develop a device that may be used to replace or repair the diseased anatomy. Morphological modeling of the affected anatomy and subsequent design of the device is enabled for printing using a 3D printer. The printed device is used either directly as an implant device, as a mold for devices requiring specific materials that cannot be printed, or as a scaffold to grow organic tissue for a bio-prosthesis. The device may be completely personalized or "semi-personalized," where the final device includes both a generic and a personalized component. Personalized devices and/or delivery systems may improve current procedural outcomes. In the case of complex anatomical deformation, as in pediatric cases, a personalized model may be the only viable option.

In another embodiment, patient-specific material properties derived from dynamic medical images are reflected in the printed object, whether used for implant or other purpose. Mechanical properties (e.g. elasticity, stiffness, or strength) of 3D printed objects are not personalized to date. Patient-specific printed objects that mimic both anatomy and material structure may help diagnosis, therapy planning, and training. Such objects may be employed to assess patient prognosis, plan surgical procedures, or even test devices before their implant.

To create a geometric model with individualized material properties of the anatomy of interest, a multi-material 3D printer is used. To create the object from medical imaging, medical images of the anatomy of interest are acquired. A detailed anatomical model of the anatomy of interest is created from the medical images. Mechanical material properties are also derived from the dynamic images of the anatomy of interest. Using the multi-material 3D printer, the object may be printed to represent the anatomy as well as material properties of the anatomy.

Figure 1:
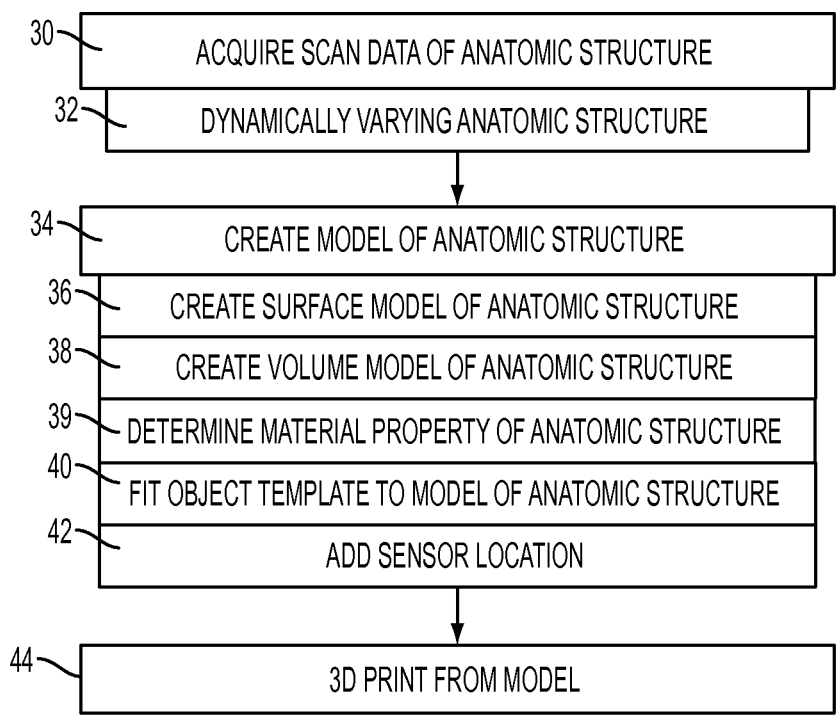
FIG. 1 is a flow chart diagram of one embodiment of a method for personalized object creation.

FIG. 1 shows a method for personalized object creation. In embodiments represented in FIG. 2, medical imaging is used for personalized implant creation. Patient specific models of the affected anatomy are extracted in act 38 from 3D imaging data acquired in act 30. The extracted surface mesh is used to generate a patient specific 3D model in act 34. The patient specific model may be further refined, such as to correct a diseased state. Using the model, a personalized device (e.g. stent) is designed and manufactured with a 3D printer, such as printing an implant in act 44. Alternatively, a mold is created to build a device with specific material that cannot be printed. In another alternative, the personalized volumetric patient model is used to create and print a scaffold in act 44 to grow organic tissue, which would be used as a bio-prosthesis. In yet another alternative, the model is used to print the delivery system of an implant.

Figure 5:
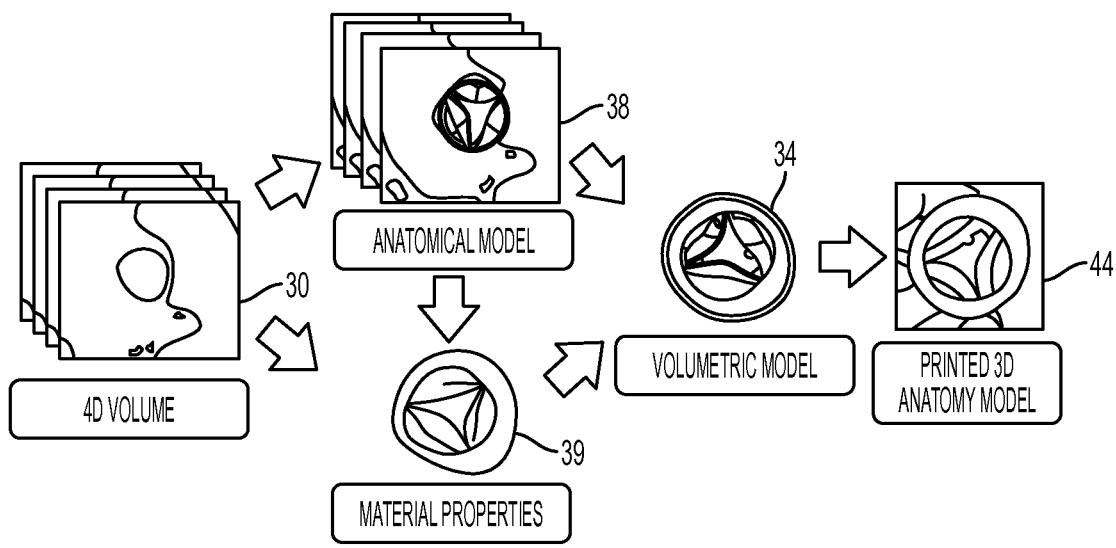
FIG. 5 illustrates an embodiment of personalized object creation using material property.

The method of FIG. 1 also includes use of material properties, which is represented by the embodiment of the method in FIG. 5. Material properties derived from the scan data and/or the anatomical model are estimated in act 39. The material properties may be used with the cardiac anatomy implant or other dynamic anatomical structure implant of FIGS. 1 and 2. Alternatively, the method represented in FIG. 5 is used for printing an implant-related object or an object to be used for diagnosis or planning.

An example below is provided for the aortic valve, but other anatomical structures may be used. There are many possible applications for designing a personalized model from medical imaging and printing an implant-related object. For example, a personalized closure device is designed and created for patients suffering from Tetralogy of Fallot (TOF). As another example, a personalized device is created for valve replacement, aortic or mitral. In yet another example, a scaffold for vascular reconstruction and exclusion of aneurysms (e.g., cerebral or AAA) is designed and created. Personalized tissue patches for valve repair or personalized devices for left atrial appendage (LAA) closure may be created.

Figure 2:
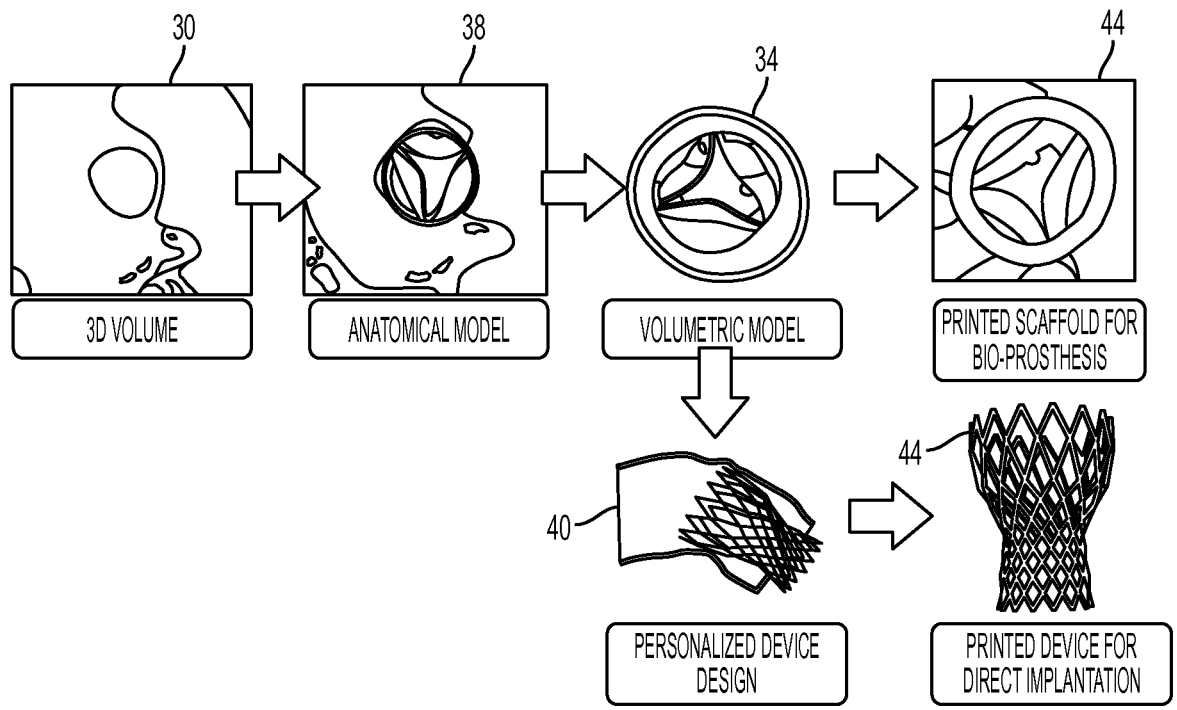
FIG. 2 illustrates embodiments of personalized object creation.
Figure 8:
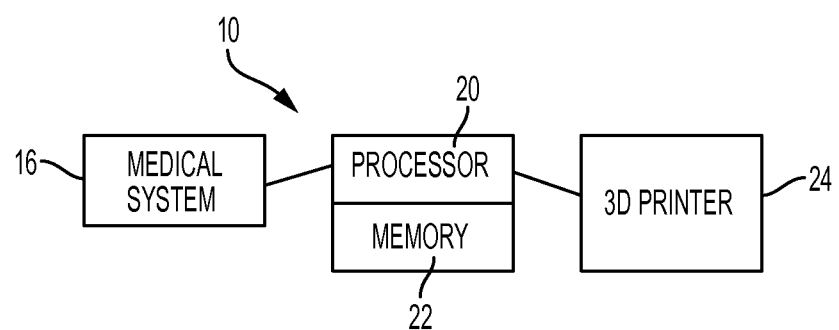
FIG. 8 is a block diagram of one embodiment of a system for personalized object creation using medical imaging.

The methods of FIGS. 1, 2, and 5 are performed by the system of FIG. 8, a processor, a medical imaging system, a different system, a 3D printer, or combinations thereof. A medical imaging scanner or a memory storing data originally acquired by a medical imaging scanner performs acts 30 and 32. A processor implements software to perform acts 34-42. The processor is part of or separate from (e.g., sever, workstation, or personal computer) the medical imaging scanner. A 3D printer performs act 44.

The method is performed in the order shown or a different order. Act 39 is performed before, after, or simultaneously with acts 36-38 and 40. Act 42 may be performed as part of act 40.

Additional, different, or fewer acts may be provided. For example, acts 32, 36, 38, 39, 40, and/or 42 are not performed. As another example, acts for converting an anatomical or other model to a 3D print model are provided. The method is one example of automated image-to-3D print, but other methods with different steps may be provided, such fitting a 3D print model or implant-related model to scan data without extracting an anatomical model from the scan data.

In act 30, scan data is acquired. The scan data is acquired by scanning a patient in three dimensions (e.g., volume scanning) with a medical imaging system. Any scanning may be used. For example, x-rays are used by a computed tomography (CT) system to scan the patient. In another example, magnetic resonance is used by a magnetic resonance (MR) imager or ultrasound is used by an ultrasound scanner. Positron emission, single photon emission computed tomography, or other scanning and corresponding imaging systems may be used. The scan data is CT, MR, ultrasound, or other scan data. Alternatively, the scan data is acquired from a memory, such as loading the scan data from a picture archiving and communications system (PACS). Data previously acquired with a medical imaging system may be loaded as the scan data.

The scan data is at any stage of processing. For example, the scan data is raw data (e.g., as a series of frames of raw data from CT, a set of k-space data from MR, or acoustic beamformed data in an acoustic grid that may be reconstructed into a volume) or data as detected from scanning the patient. As another example, the data is processed, such as filtered or image processed. The scan data may be processed to be a set of voxels, point data, or segmented meshes. The scan data may be image data. Image data may refer to an actually displayed image or to the frame of data that may be used for generating the display.

The scan data is acquired as a frame of data. Other groupings than frames may be used. The frame of scan data represents a region (e.g., volume) within a patient. The region includes any anatomic structure, such as an organ, tissue, bone, or vasculature. In one embodiment, the scan data represents a cardiac structure, such as a valve, vessel wall, or part of a heart. Other non-anatomic structures may be represented, such as an implant or catheter. The region may include only part of one or more anatomic structures. By scanning the region, data representing anatomy is acquired. Any anatomic structure may be represented.

In one embodiment, the anatomic structure is subjected to stress, strain, or other force causing variation in the shape, size, position, or other characteristic over time. A physiological cycle, such as the heart or breathing cycle, may cause variation of the anatomy over time. The scan data is acquired in act 32 by scanning the dynamically varying anatomic structure.

To deal with the variation, the scan data may be acquired to represent the anatomy at one phase of the cycle. Triggering or gating is used to acquire the frame of scan data to represent the anatomy at the desired phase. For example, a heart valve changes size, position, and internal arrangement over the heart cycle. Triggering may be used to acquire scan data representing the valve at the R-wave or S-wave of the heart cycle. Alternatively, a sequence of frames of data representing the anatomy over time is acquired. The sequence may indicate the variation of the anatomy. One frame in the sequence may be used, or multiple frames may be used to determine an average or other statistical shape. By repeating the scanning, the anatomy over time may be represented, providing the dynamic variation of the anatomic structure over time.

The patient may have a disease. The scanned anatomy may not have a normal or non-diseased shape, size, material property, or other characteristic. The scanned anatomy may have additional material. The diseased state is reflected in the scan data. In alternative embodiments, the anatomy is healthy or operates incorrectly despite being normal as reflected in the scan data.

In act 34, a model of the anatomic structure is created from the scan data. The creation uses segmentation to define a surface in act 36, expansion of the surface to a volume model in act 38, determination of other characteristics of the model (e.g., material property) in act 39, and fitting a template of the object to be printed to the anatomic model in act 40. Acts 36-40 provide one approach for creating the model. Other approaches may be used, such as fitting a template model to scan data without surface or volume segmentation or using the anatomic or volumetric model without further fitting of a template of the object to be printed.

In act 36, a processor creates a surface of the anatomic structure based on the scan data. Any technique for identifying a surface of anatomy may be used. For example, segmentation is used. Alternatively, the surface geometry of the patient specific model of the anatomy of interest is estimated from the scan data using a physiological template model. The patient specific parameters of the physiological template model are estimated from volumetric 3D images with robust machine learning algorithms using hierarchical approaches within the marginal space learning (MSL) frameworks. Detectors are successively trained using the probabilistic boosting tree (PBT) with Haar, steerable features, and/or other features. The machine-learnt classifier is applied to the scan data to estimate the rigid object parameters (bounding box estimation) followed by the anatomical landmarks and then the surface structures in a hierarchal manner. Other machine learning may be used, with or without a hierarchal analysis. As an alternative to applying a machine-learnt classifier for a physiological model, a shape model, such as a mean shape model, is fit to the data using any warping or fitting. Automated, semi-automated, or manual fitting may be provided.

In one embodiment, frames from different times are used to create the surface. By applying the machine-learnt classifier or other fitting over time, a surface for a given time may be more accurately determined. A spring, magnet, distance or other cost function may be applied over time to prevent large or unexpected deviation in the surface over time. A frame of reference or the surface at a particular time is chosen for further processing, but the surface for that frame relies on the scanned anatomy of other times. More than one frame or scan data representing more than one time may be selected, such as to create printed objects for different times.

Figure 3:
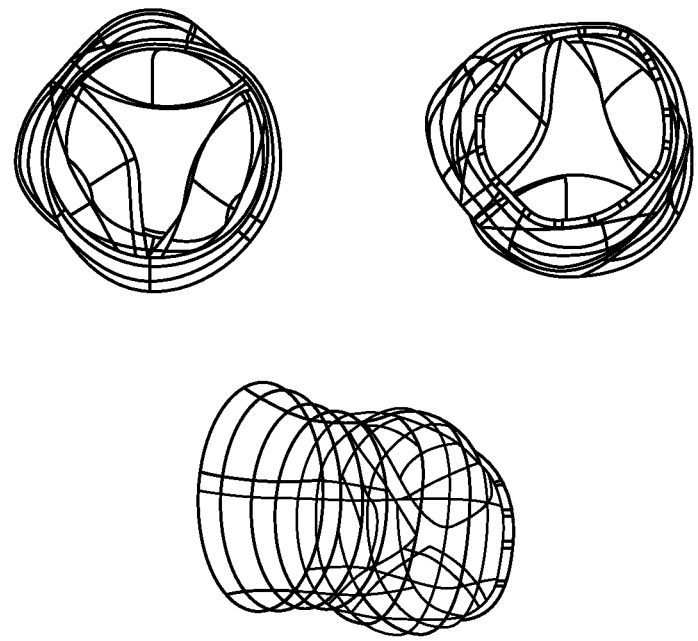
FIG. 3 shows an example anatomical surface for a valve of a patient.

FIG. 3 shows an example of a surface identified by a machine-learnt classifier locating the surface of an aortic valve in 3D CT data. The valve and corresponding created surface as a mesh are shown in top, bottom, and side views. The surface includes the aortic valve root and three leaflets. Other structures may be included, such as chordae. Machine-learnt classification may be better able to handle the very small structure of the valve. Other segmentation or surface identification may be used for larger or less dynamic structures.

Figure 4:
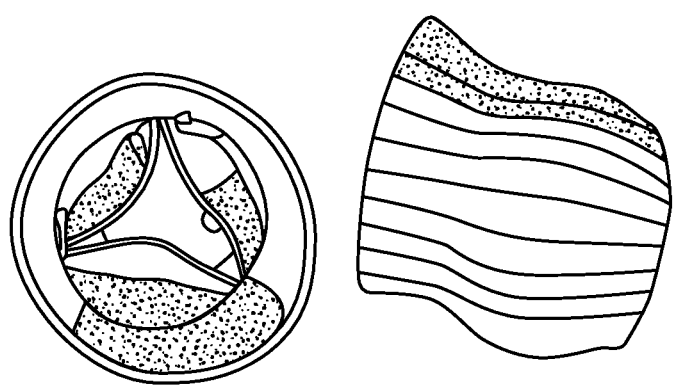
FIG. 4 shows an example volume model for anatomy of patient.

In act 38, the processor expands the surface into a volume. As expanded, the volume is a model of the anatomy. For smaller or other anatomy, segmentation of the anatomy as a volume may be difficult based on the resolution of the scan data. Instead, the surface is used as a starting point. The volumetric model is constructed from the surface anatomy by extruding the surface along normals to the surface. FIG. 4 shows a volumetric model example for the aortic valve.

Any thickness or amount of extrusion may be used, such as based on an atlas or mean measure of the anatomy. In one embodiment, the user inputs the thickness. In another embodiment, the thickness is estimated from the scan data. The thickness is constant or may vary over the model, such as the aortic root being thicker than the leaflets. The extrusion is in any direction, such as inward relative to the anatomy.

In alternative embodiments, volumetric segmentation is provided with or without also creating the surface. The scan data is used to segment out or identify the volumetric shape of the anatomy. In yet other embodiments, a mean shape model or other template is fit to the scan data, so the mean shape model or other template provides the volumetric model or extent as part of the mean measures and/or part of the fitting.

The volumetric model represents the anatomic structure of the patient. This anatomical model is created from the scan data of that patient, so has a size, shape, and/or other characteristics specific to the given patient. The volume model of act 38, segmented from the scan data, provides a model of the anatomic structure of act 34.

The volumetric model may be altered. For example, the model reflects disease of the patient, such as a tear, hole, missing part, or inflamed or oversized part. As the model derived from patient-specific scan data contains abnormalities, the physician is able to manually refine the volumetric model. Any user interface for alteration of the extracted volumetric model may be used. Alternatively, a processor identifies the abnormality and performs the correction. For automated repair, the volume model may be compared to a mean shape model. Sufficiently different structure or deviation is replaced with the mean shaped model.

Where an implant is to be provided to fix or mitigate the problem, the model may be altered to remove, reduce, or counteract the disease. For example, a virtual repair is performed on the model to correct the disease. The virtual repair is handled manually by the physician or may be automated. In one example, a patient with a congenital disease is scanned, so the resulting volume model created from the scan data includes the congenital defect. The defect is repaired in the model.

In act 39, other characteristics of the model are determined. The volume model indicates volume and shape, but not material properties. For example, the model may not indicate an elasticity or stiffness of the tissue represented by the model.

Different parts of the anatomy may have different elasticity. FIG. 4 shows shading of the aortic valve where the shading is modulated by the tissue stiffness. Some parts of the model have greater stiffness than other parts. The material property value may be homogeneous (same value everywhere in the model), heterogeneous (spatially varying) or dynamic (time-dependent to capture active processes observed in living organs, like during cardiac contraction). This variation in one or more material properties may be added to the model, such as a flag or field for each voxel, node, or part of the model indicating the local value of the material property or properties.

Any source of material property for the volumetric model may be used. An atlas indicates the property for different parts of the anatomy. In another embodiment, a template fit to the scan data as the model may include representative values for the material property. Combinations of different approaches may be used, such as by averaging.

To provide more patient-specific values for the material property, the processor estimates the mechanical properties of the anatomy from the scan data. In one embodiment, the property is measured by medical scanning, such as using elasticity ultrasound imaging. Direct measurement may be used.

In another embodiment, the property is measured using a dynamic model representing the anatomy of interest. As represented by the arrows in FIG. 5, the anatomical model, such as an optimized biomechanical model, may be used to derive the material properties. A spatially varying material property map of the anatomy is based on the dynamic model of the anatomy of interest and the underlying image information. An inverse modeling framework is used. The inverse modeling framework uses an iterative optimization technique, such as a gradient-free approach like Bound Optimization by Quadratic Approximation (BOBYQA), to estimate the tissue parameters on the anatomy of interest. Any optimization to determine the spatial and/or temporal distribution of the values of the material property may be used. A computation model (e.g. biomechanical template) of the anatomy mimics the organ physiology and is controlled or parameterized by any number of parameters, such as stiffness as a global, regional, or local parameter. The optimization attempts to solve for the values of the parameters based on a comparison of the computational model given different parameter values with the scan data. When a specific parameter set is identified as a best or sufficient match, the computational model simulates the organ function over time. As the anatomy is observed in the dynamic image sequence, the fit of a given set of parameters may be evaluated. Any measure of fit may be used, such as computing a mesh difference between the simulated sequence and the observed. The resulting optimized parameter set provides the estimate of the values of the material property.

In another embodiment, the values for the material property or properties are estimated using learning based tissue parameter estimation. For example, the stiffness is estimated indirectly from the observed motion using a machine-learnt classifier. The learning-based framework does not use an iterative optimization method to estimate the tissue properties for regions of the anatomy of interest but rather directly regresses the values for the tissue property from features extracted from the observed dynamic image sequence (e.g., scan data over time). A regressor, such as Randomized Trees, SVM, polynomial regression, or simple nearest neighbor approach is used for training the classifier. Based on a set of training data, the regressor is trained with features derived from the image (e.g., Haar or steerable) or the geometrical models over space and time. The material properties needed for supervised training are generated from an inverse modeling framework, atlas, physical measures from biopsied anatomy, or other source. For a given patient, the trained classifier estimates the values of the material property from feature values extracted from the scan data.

Once the values of the material property or properties are estimated, the values are added to the volumetric model. The created volumetric model contains both the anatomy and the tissue properties for the anatomy of interest. For the aortic valve example, the stiffness values for each region of the anatomy of interest are based on the stiffness map of any resolution. The estimated stiffness map may be either surface-based or volumetric. If the stiffness map is surface-based, then the volumetric stiffness map is obtained by extrapolation or known relationship of surface stiffness to stiffness away from the surface. If the stiffness map is volumetric, the values are directly mapped to the volumetric model.

In act 40, the processor is a template to the anatomic structure as represented by the scan data. The template is of the implant-related device or the object to be printed. For example, a scaffold or mold is to be printed. A template of the scaffold or mold is fit to the volumetric model, creating a personalized object to be printed. Where the volumetric model, such as altered to remove a disease state, represents the implant itself, template fitting may (e.g., fit a 3D print model to the anatomical or volumetric model) or may not be provided.

Figure 6:
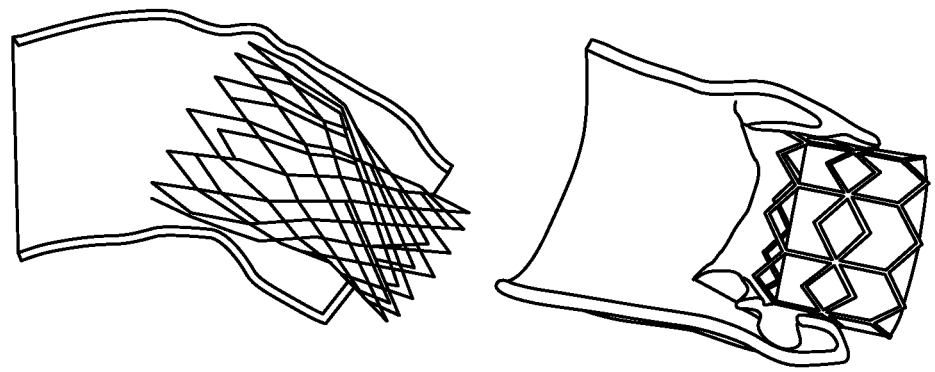
FIG. 6 shows an example implant or scaffold relative to an anatomy model.

Based on the volumetric model, various options may be used to construct a personalized or semi-personalized device. In one option, the device is designed based on the geometric model of the anatomy of interest. FIG. 6 shows an aortic valve with two different implants. These stents or other implants are fit to the volumetric model. Any characteristic may be fit, such as the diameter, length, surface shape, hole size, curvature, pattern, and/or wire stiffness. Computer-aided design (CAD) systems may be used to model the implant-related device, which is fit to the anatomical model. A variation of this option is to use a library of devices and select one template to be interactively deformed to fit the specific anatomy of the patient. A computational model may be used to develop a patient specific design, such as to optimize the device in respect to the stress on the material and/or fit to avoid leaking.

Any implant-related device may be fit to the anatomical model. Implant-related devices include an implant itself, whether a replacement of the anatomy (e.g., replacement valve), a stent, or other object to be placed within the patient. Implant-related devices include a scaffold or other structure used for growing tissue for a bio-prosthesis. A mold to create the implant is an implant-related device. A delivery device to perform an implant is an implant-related device.

The template for the object may include 3D printer-specific structure, such as a base or orientation for printing the object. Alternatively, a user adds the structures. The resulting object or device is converted to or is already in a format for 3D printing. Any conversion from the model to a 3D print file may be used. The model may be converted to a CAD file, where any alterations are made, and then converted to a 3D print model usable by a 3D printer.

In act 42, the model as formatted as a mesh or for 3D printing is designed to include a sensor structure. For example, a space for fitting or holding a sensor, transmitter, battery, or combinations thereof is added to the model. For a template, the template may include the space for the sensor structure.

The sensor or sensors are to be embedded in the generated device. The sensor is either directly printed with the implant-related device or embedded after printing. The sensors may be used to monitor biomarkers (e.g., pressure, stress, flow, temperature, or strain) relevant to diagnose malfunction of the device and/or acute problems of the patient. The sensed data may then be wirelessly transmitted to a receiver device outside the patient.

In act 44, the 3D print model is 3D printed. The model may be reformatted or compiled into instructions for printing. Alternatively, the model includes the compiled instructions. In response to the model, the 3D printer prints out a plastic, metal, paper, or other material representation of the anatomy of the patient or implant-related device. One or more parts, such as the base or added support structure, may be removable or colored differently. For example, added support is printed in a clear or partially transparent material while the anatomy is printed in one or more other, more opaque colors. The base is removable, such as by clipping.

The object, such as the anatomy, is printed. In one embodiment, an implant-related device is printed. The printed object is based on the model of the anatomic structure of the patient, so is personalized in size, shape, and/or material property to the patient.

There are different options for printing an implant-related device. The selection of one of the options may depend on the anatomy of interest, the patient disease or defect, a physician's choice, and/or the most effective corrective procedure.

Figure 7:
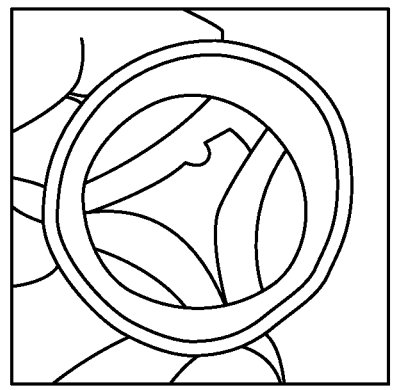
FIG. 7 shows an example printed valve or scaffold for bio-prosthesis.

In one option, the implant itself is printed. A personalized implant is sized and shaped to the patient. The implant is a replacement, such as a replacement valve. For example, a valve as shown in FIG. 7 is built as a replacement valve. Alternatively, the implant is a support structure, such as a stent or scaffold shown in FIG. 6. A scaffold is sized or shaped to promote tissue in-growth once inserted into the patient. Other support structures may be a patch or other shape. The fitted template model or anatomical (volumetric) model altered to fix a defect may be directly manufactured with a 3D printer.

A partially or semi-personalized implant may be printed. Part of the template model may be generic, such as being of a given shape, size, or other characteristic. Another part may be personalized, such as altering the shape or size of one end of the implant but leaving the other end of the implant as a generic shape or size usable in a range of patients. In the case of semi-personalized devices, the manufactured personalized component is combined with a generic part, constituting the final, printed device.

In another option, a scaffold for a bio-prosthesis is printed as the implant-related device. Rather than relying on tissue growth inside the patient, a scaffold for tissue growing outside the patient is printed. For example, the volumetric model is printed as shown in FIG. 7 to be used for growing tissue fitted to the valve of the patient. The bio-prosthesis resulting from growing tissue in or on the scaffold is then implanted.

The size, shape, material, and/or other characteristic (e.g., hole size and shape or grid pattern) of the scaffold is personalized to the patient. The scaffold is created using 3D printing from the previously constructed volumetric or fitted template model.

In one embodiment, the selection of a specific scaffold is based on a database of cases. Based on the disease, the processor finds the N most similar cases from the past sorted based on outcome (e.g., best outcomes would appear first). The physician or processor then decides which is the most applicable case. The scaffold used in the selected case is altered to account for the patient, such as altering a size. Alternatively, the selection is based on a match in size, shape, and/or defect, so the selected scaffold is personalized without further change. The resulting template is used for 3D printing. This procedure may be useful for congenital replacement or repair procedures where each case is unique.

In another option, the implant-related device is a mold for making the implant. The volumetric model or the fit template is used to create the mold. The printed mold is used to build a device with specific material that cannot be printed. The 3D printer builds the mold, which is then used to build the implant.

In yet another option, bio-printing is used. Tissue or tissues are deposited to biologically print the implant or part of the implant. The printed object may be free of a scaffold, instead binding tissue to itself. For example, a scaffold-free organ is directly printed from the volumetric or fitted template model with a 3D bio-printer. The model may be decomposed into several tissue types present in certain regions of the anatomy (e.g. tissue type based on density, structure stability, or other characteristic). Alternatively, a scaffold is used or printed as well as the tissue with a multi-material 3D printer.

To print tissue, any now known or later developed technique may be used. Biomimicry (e.g., the printing of cellular functional components of tissues (replication of biological tissues on a micro-scale)), autonomous self-assembly, or mini-tissues printing may be used. Inkjet, microextrustion, and/or laser-assisted bio printing may be used.

Combinations of the options may be used. For example, an implant with a bio-printed part and a scaffold part is printed. As another example, a scaffold is 3D printed for joining to a device made from a printed mold.

In other embodiments, the template or volumetric model is used to print a delivery device. The delivery device is a catheter, needle, scope, or other structure for insertion into the patient. The delivery device is implant-related by being used to implant another device. Alternatively, the delivery device includes a treatment tool, such as an electrode, scalpel, or forceps.

The volumetric model may provide a bend or other shape consideration for implanting. The template model of the delivery device may be fit to the volumetric model. In either case, the delivery device may be pre-disposed (e.g., shaped) or sized for delivery of a generic or personalized implant to the patient. The delivery device is personalized in some characteristic to the patient and 3D printed. The delivery device may be personalized to any anatomy, such as the anatomy to be treated or anatomy through or along which the delivery device passes (e.g., minimal incision or natural orifice entry point).

In another embodiment, the printed object is not related to the implant. For example, the volumetric model is printed to assist in diagnosis, therapy testing, or planning purposes. In the valve example, the valve as represented by the model is printed as shown in FIG. 7. This personalized representation of the valve of the patient may be used for any purpose.

An implant-related device or object used for any purpose may be printed with multi-material printing. Where one or more tissue properties are incorporated into the model, the 3D printing may mimic the tissue property. Different materials used by the 3D printer may have different values for one or more material properties. The different materials are used for different locations in the printed object. For further resolution of the material property, different mixes of the different materials may be used for different locations.

The differences in material properties of the anatomy or template model are mapped to the differences in the material properties of the materials used for printing. For example, the materials used for printing may have a same range of stiffness as measured for the anatomy, so a 1-to-1 mapping is used. As another example, the ranges are different, so the object is printed to have a similar variation in stiffness, but different absolute stiffness. The resulting printed object represents the different material properties of the anatomy.

FIG. 5 shows one example use of the material property measurement (act 39). The material properties are used with the anatomical model (act 38) to create the final volumetric model (act 34). The volumetric model includes the material property variation. The volumetric model is converted to a 3D print format and printed in act 44. The printing uses the material property information to provide an object with variation in material property similar to or emulating the variation for the patient.

FIG. 4 shows a system 10 for personalized implant or other object creation from medical scan data. The method of FIGS. 1, 2, 5 or another method is implemented by the system 10. In general, the system 10 processes 3D or 4D imaging data to extract a patient specific model (manually or automatically). The patient specific model is used to create an implant-related device for 3D printing. In a further embodiment, the system 10 estimates tissue properties of the anatomy of interest based on dynamic patient specific models extracted from 4D scan data and/or estimates from the scan data itself. Spatially varying material property or properties are estimated. The system 10 combines the anatomical model and estimated material properties, creating a volumetric model for printing. The system 10 prints the model using multi-material 3D printers so that the resulting object emulates the material property of the anatomy.

The system 10 includes a medical imaging system 16, a processor 20, a memory 22, and a 3D printer 24. Additional, different, or fewer components may be provided. For example, a network or network connection is provided, such as for networking with a medical imaging network or data archival system. As another example, a user interface is provided. In yet another example, the medical system 16 is not provided. The data representing the patient is obtained from the memory 22. In other examples, a display is provided for displaying the model of the anatomy or images derived from the scan data.

The processor 20 and memory 22 are part of the medical imaging system 16 or other system. Alternatively, the processor 20 and/or memory 22 are part of an archival and/or image processing system, such as associated with a medical records database workstation or server. In other embodiments, the processor 20 and/or memory 22 are a personal computer, such as desktop or laptop, a workstation, a server, a tablet, a network, or combinations thereof.

The medical system 16 is any now known or later developed medical imaging system or scanner. For example, the medical system 16 is a computed tomography or other x-ray system (e.g., fluoroscopic). An x-ray source and detector are positioned opposite each other and adjacent to a patient and may be moved about the patient for scanning. In one embodiment, the medical system 16 is a spiral or C-arm computed tomography system. In other examples, the medical system 16 is a magnetic resonance, positron emission, ultrasound, single photon emission computed tomography, or other imaging system for scanning a patient.

The medical system 16 is configured by stored settings and/or by user-selected settings to scan a patient or a portion of the patient. The scan occurs by transmitting and receiving or by receiving alone. By positioning relative to the patient, aiming, and/or detecting, the anatomy is scanned. For example, the heart is scanned. The scanning may be repeated to scan the patient over time, such as scanning to acquire multiple frames of scan data representing the patient at different times throughout a physiological cycle. By scanning over time, changes in the anatomy due to the cycle may be captured. Other information, such as from other anatomy, may or may not be acquired as well.

The memory 22 is a graphics processing memory, video random access memory, random access memory, system memory, cache memory, hard drive, optical media, magnetic media, flash drive, buffer, database, combinations thereof, or other now known or later developed memory device for storing scan data. The memory 22 is part of the imaging system 16, a computer associated with the processor 20, a database, another system, a picture archival memory, or a standalone device.

The memory 22 stores the scan data representing a region of a patient. Multiple frames of data representing the patient over time may be stored, or a frame of voxel data representing the patient at one time is stored. The region is a three-dimensional region. The region is of any part of the patient, such as a region within the chest, abdomen, leg, head, arm, or combinations thereof. The scan data is from scanning the region. The data represents the anatomy in the region.

The memory 22 may store processed data. For example, filtered scan data, image processed data, segmentation, created mesh, surface model, volume model, template model, material properties, and/or 3D printer model are stored.

The memory 22 or other memory is alternatively or additionally a computer readable storage medium storing data representing instructions executable by the programmed processor 20 for creating a 3D printer model from medical scan data. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts, or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 20 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for creating a patient-specific 3D print model from image or scan data of the patient. The processor 20 is a single device or multiple devices operating in serial, parallel, or separately. The processor 20 may be a main processor of a computer, such as a laptop or desktop computer, or may be a processor for handling some tasks in a larger system, such as in an imaging system. The processor 20 is configured by instructions, design, firmware, hardware, and/or software to be able to perform the acts discussed herein.

The processor 20 is configured to segment structure of the patient from the scan. Data representing the volume or volume over time is processed to find locations and/or surfaces of anatomic structures or parts of anatomic structures. Any segmenting may be used. The segmentation is automatically performed without user input to indicate anatomy locations, or user input may be used to assist in the segmentation.

The segmenting itself provides a surface or mesh for the anatomy. Alternatively, the located anatomy is used to create the mesh or surface. The processor 20 creates a surface model of the anatomy of the patient from the scan. A volumetric model is constructed by the processor based on the surface model. The surface model is expanded to define the volumetric model. In other embodiments, the segmentation by the processor provides a volumetric model. In yet other embodiments, the processor 20 fits a volumetric template of the anatomy to the patient-specific scan data. The fitted template provides the volumetric model. The fitting may be by spatial correlation and/or optimization of parameters defining a physics-based template model.

While the model may be used for 3D printing without material property information, in another embodiment, the processor 20 is configured to estimate variation of one or more material properties. The estimation is based on dynamic behavior of the anatomy, such as change represented by the scans. For example, the variation in material property is estimated with inverse modeling by optimizing values of one or more parameters of a physics-based model to the match the scan data over time. As another example, features are extracted from the scan data from different times to estimate the variation in the material property using a machine-learnt classifier. In alternative embodiments, the scan itself provides a measure of the material property, such as a measure of elasticity. The variation of the material property is added to the volumetric or template model.

The processor 20 is configured to create a model for 3D printing from the volumetric model or fitted template model. The 3D print model may be created directly by converting the volumetric or fitted template model. Alternatively, the fitted template is formatted as or includes the conversion to the 3D print format.

The processor 20 may be configured to generate an image for display, such as display of the volumetric model. A three-dimensional rendering of the scan data for locations of the anatomy is generated. An image of the scan data without segmentation or using segmentation for relative highlighting may be generated. Alternatively or additionally, an image of the volumetric model, fitted template, or other model for three-dimensional printing may be generated.

The 3D printer 24 is any now known or later developed 3D printer. A reservoir of plastic, metal, or other material connects with a deposit head. Multiple reservoirs for different materials may be provided. Under the control of a controller, the deposit head(s) and/or a support platform are moved to add successive material in layers, building up the three-dimensional construction until a physical model of the three-dimensional print construction is created. Any additive manufacturing system may be used.

The controller of the 3D printer 24 receives 3D printer formatted model or instructions to print the object based on the volumetric model. The implant-related (e.g., implant, mold, scaffold, tissue structure, or delivery device) object is printed. In other embodiments, an object related or not related to implanting is printed, such as printing a model of anatomy for planning, diagnosis, or other purpose.

In one embodiment, the 3D printer 24 is a multi-material 3D printer. The controller causes selection and deposit of different materials and/or combinations of materials to print the object. Different parts of the object are printed with different materials to emulate a material property variation of the anatomy. The print materials are mapped from material properties of the anatomy of the patient so that the printed object emulates the variation of the material property of the patient.

The printed object with variation in material property may be used in various applications. The printed object may be used in the areas of diagnosis, planning, guidance of therapy, or training. In the case of aortic valve therapy for instance, the printed object may be used for a hands-on approach towards trans aortic valve implantation (TAVI) planning. For mitral valve for instance, the printed object may be used to test new devices or to devise the optimal surgical procedure, in particular if the printed object also incorporates the chordae. Different implant devices and device types may be placed within the 3D printed object to assess the impact of implant over and under sizing. Especially for patients with abnormal valve shapes, this use for planning or assessing the impact of a specific device on the patient may avoid insertion of less effective implants. Implant manufacturers may utilize the printed object within mechanical simulators to verify the efficacy of their devices on a wide variety of realistic anatomical models.

While a valve example is used herein, any anatomy may be used. For example, vessel, other part of the heart, kidney, stomach, liver, or brain may be modeled and a personalized object printed.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for personalized implant creation, the method comprising:
acquiring, from a medical imaging system, image data representing an anatomic structure of a patient, the image data representing the anatomic structure dynamically varying over time in response to a physiological cycle of the patient, the physiological cycle comprising a heart or breathing cycle applying force to the anatomic structure causing the dynamic variation over time;
creating a bio-mechanical model of the anatomic structure from the image data and the dynamic variation over time including a change in shape, size, or position of the anatomic structure;
deriving material properties of the anatomic structure from the bio-mechanical model including stiffness, elasticity, and strength of different locations of an organ, tissue, bone, or vasculature of the anatomic structure;
mapping differences in the derived material properties of the anatomic structure to material properties of printing materials for a three-dimensional printer; and
printing with the three-dimensional printer a personalized implant for implantation into the patient based on the bio-mechanical model of the anatomic structure of the patient using printing materials such that the personalized implant reflects the stiffness, elasticity, and strength of the anatomy of the patient.

2. The method of claim 1 wherein acquiring comprises acquiring the image data where the anatomic structure is part of a cardio-vascular system of the patient, the acquiring being for a first phase of the physiological cycle.

3. The method of claim 1 wherein acquiring comprises acquiring the image data where the anatomic structure is a valve, vessel, or heart wall.

4. The method of claim 1 wherein acquiring comprises acquiring the image data where the anatomic structure is diseased, and wherein creating the model comprises altering the model to account for repair of the anatomic structure.

5. The method of claim 1 wherein creating the model comprises creating a surface of the anatomic structure based on the image data and expanding the surface into a volume, the volume being the model.

6. The method of claim 1 wherein printing comprises printing the personalized implant as a scaffold sized, shaped, or sized and shaped to the model, the scaffold being a base for tissue growing of a bio-prosthesis.

7. The method of claim 1 wherein printing comprises printing the personalized implant as a biological printing of tissue.

8. The method of claim 1 wherein printing comprises printing the personalized implant as a delivery device of the implant.

9. The method of claim 1 further comprising including a sensor structure in the personalized implant.

10. The method of claim 1 wherein creating the model comprises fitting a template to the anatomic structure as represented by the image data.

11. The method of claim 1 wherein the model includes different parts with different material properties, and wherein printing comprises multi-material printing the personalized implant to include representation of the different material properties.

12. The method of claim 1, wherein the material properties are derived from the image data using machine learning based tissue parameter estimation.

13. The method of claim 12, wherein the machine learning based tissue parameter estimation regresses the values for a tissue property from features extracted from an observed dynamic image sequence in the image data.

14. A system for personalized implant creation, the system comprising:
a medical imaging system configured to scan a patient and acquire image data representing an anatomic structure of the patient, the image data representing the anatomic structure dynamically varying over time in response to a physiological cycle of the patient, the physiological cycle comprising a heart or breathing cycle applying force to the anatomic structure causing the dynamic variation over time;
a processor configured to create a three-dimensional surface model of the anatomic structure from the image data and the dynamic variation over time including a change in shape, size, or position of the anatomic structure, and construct a volumetric model based on extrusion from the three-dimensional surface model, the extrusion adding thickness to a surface of the three-dimensional surface model to form a volume of the volumetric model, derive material properties of the anatomy of the patient from the dynamic variation of the volumetric model over time, and map differences in the derived material properties of the anatomy to material properties of printing materials for a multi-material three-dimensional printer; and
the multi-material three-dimensional printer configured to print an object for implantation into the patient with different parts comprising different materials to emulate a material property variation of the anatomy derived from the dynamic variation.

15. The system of claim 14 wherein the multi-material three-dimensional printer is configured to print the object as the implant, a mold, a scaffold of a bio-prosthesis, or as tissue.

16. A system for personalized object creation, the system comprising:
a medical imaging system configured to scan a patient at different times of a physiological cycle where anatomy dynamically varies between the different times in response to a physiological cycle of the patient, the physiological cycle comprising a heart or breathing cycle applying force to the anatomic structure causing the dynamic variation over time;
a processor configured to construct a volumetric model including the dynamic variation and estimate variation of a material property of the anatomy based on the dynamic variation over the physiological cycle represented in the volumetric model, the variations of the material properties being of values of the material property as a function of locations of the same organ, tissue, bone, or vasculature such that different locations have different values of the material property;
the processor configured to map differences in the estimated variations of the material properties of the anatomy to material properties of printing materials for a multi-material three-dimensional printer; and
the multi-material three-dimensional (3D) printer configured to print a personalized object for implantation into the patient using different materials in the object, the variation of the different materials emulating the variation of the material property of the anatomy.

17. The system of claim 16 wherein the material property comprises elasticity, and wherein the processor is configured to estimate the variation with inverse modeling or a machine-learnt classifier.

18. The system of claim 16 wherein the processor is configured to create a model of the anatomy where the model includes the variation of the material property.

* * * * *